United States Patent [19]

Jönsson et al.

[11] 4,292,324

[45] Sep. 29, 1981

[54] AQUEOUS ZINC SOLUTIONS FOR MEDICAL USE

[75] Inventors: Karl E. Jönsson, Lund; Nils F. E. Moren, Staffanstorp, both of Sweden

[73] Assignee: Aktiebolaget Draco, Lund, Sweden

[21] Appl. No.: 22,208

[22] Filed: Mar. 19, 1979

Related U.S. Application Data

[63] Continuation of Ser. No. 849,174, Nov. 7, 1977, abandoned, which is a continuation-in-part of Ser. No. 845,367, Oct. 25, 1977, abandoned, which is a continuation of Ser. No. 71,720, Apr. 25, 1975, abandoned.

[30] Foreign Application Priority Data

May 2, 1974 [SE] Sweden .............................. 7405839

[51] Int. Cl.$^3$ ........................................... A61K 31/315
[52] U.S. Cl. .................................. 424/289; 424/145; 424/317
[58] Field of Search ........................................ 424/289

[56] References Cited

U.S. PATENT DOCUMENTS

| | | | |
|---|---|---|---|
| 2,811,483 | 10/1957 | Aterno et al. | 424/280 X |
| 2,904,573 | 9/1959 | Oroshnik | et al./260 |
| 3,463,858 | 8/1969 | Anderson | 424/289 |
| 3,480,715 | 11/1969 | Catsch | 424/289 |
| 3,501,577 | 3/1970 | O'Neill | 424/289 |
| 3,647,834 | 3/1972 | Martin | 260/429.9 |
| 3,887,704 | 6/1975 | Lichtenstein | 424/145 |
| 3,941,818 | 3/1976 | Abdel-Monem | 260/429.9 |

FOREIGN PATENT DOCUMENTS

2013426 10/1971 Fed. Rep. of Germany .

*Primary Examiner*—Leonard Schenkman
*Attorney, Agent, or Firm*—Brumbaugh, Graves, Donohue & Raymond

[57] ABSTRACT

A pharmaceutical composition containing zinc in the form of one or more water soluble zinc salts and a complex-former selected from the group consisting of hydroxycarboxylic acids, acid anhydrides, or salts thereof. The water solutions thereof give a palatable, acceptable peroral zinc solution and are useful for treating leg ulcers, post-operative wounds, decubital ulcers and other diseased conditions in zinc anemia.

5 Claims, No Drawings

AQUEOUS ZINC SOLUTIONS FOR MEDICAL USE

The instant application is a continuation of application Ser. No. 849,174 filed Nov. 7, 1977 which is a continuation-in-part of application Ser. No. 845,367, filed Oct. 25, 1977, which is in turn a continuation of application Ser. No. 571,720, filed Apr. 25, 1975 all now abandoned.

BRIEF SUMMARY OF THE INVENTION

The present invention relates to a process for preparing a pharmaceutical preparation containing zinc having improved tolerance and intended to give a palatable, acceptable peroral zinc solution and such a penetration, and its use in therapy.

The object of the present invention is to obtain a zinc containing pharmaceutical preparation intended for zinc therapy, which preparation has been made palatable by eliminating the astringent taste deriving from zinc.

Common zinc salts such as zinc chloride, zinc nitrate, zinc sulphate, zinc carbonate, and zinc acetate all have very astringent tastes in aqueous solutions. Zinc in solution has thus not been able to replace other solid preparations to any great extent due to its astringent taste.

During the 1950's it was verified that zinc has a positive effect on wound healing in animals. Subsequently it has been shown the rate of wound healing increases by about 50% if zinc is given to zinc anemic persons.

In case of dwarfism, hypoganadism and a number of diseased conditions it has also been verified that a very low zinc level exists in the blood.

The greatest use of zinc is, however, related to wound healing as the healing of i.e. leg ulcers, decubital ulcers, burns and post-operative wounds.

In zinc treatment, solid preparations as mentioned above have been used. These develop on the other hand gastrointestinal disturbances which may be so serious that the treatment must be interrupted.

Zinc pastes and zinc ointments have also been used locally on leg ulcers.

Surprisingly, it has now been shown possible to eliminate these drawbacks by the present invention which is characterized in that one or more water-soluble zinc salts are added to a complex-former selected from the group consisting of $\alpha$-hydroxycarboxylic acids or acid anhydrides or salts thereof, the relation between complex-former: zinc being at least equimolecular, and a pH-regulating agent is added in such an amount that the pH of an aqueous solution of the preparation is 3 to 9.

According to the invention an $\alpha$-hydroxycarboxylic acid is used, i.e. a carboxylic acid having a hydroxy group in $\alpha$-position to the carboxylic acid group.

According to a suitable embodiment of the invention an $\alpha$-hydroxycarboxylic acid selected from the group consisting of citric acid, tartaric acid, malic acid, lactic acid and glycolic acid is used.

According to a further suitable embodiment of the invention the water-soluble zinc salt is selected from the group consisting of zinc chloride, zinc sulphate, zinc nitrate, zinc acetate, and zinc carbonate.

According to another, further suitable embodiment of the invention the amount of zinc is 3 to 500 mg per peroral dosage unit.

According to another suitable embodiment of the invention pH regulating agents are added in such an amount that the pH is 3 to 6, after dissolving the preparation in water.

According to the invention the preparation is prepared in the form of effervescent tablets, tablets, effervescent powders, or powders, which are intended to be dissolved in water prior to administration, or in the form of carbonized or non-carbonized aqueous solutions.

According to a further aspect of the invention it is also related to a pharmaceutical preparation containing zinc, which is characterized in that zinc is present as a complex with a carboxylic acid selected from the group consisting of hydroxycarboxylic acids, acid anhydrides, or salts thereof, the relation between complex-former: zinc being at least equimolecular, and having an addition of a pH regulating agent in such an amount that the pH is 3 to 9 in an aqueous solution of the preparation.

DESCRIPTION OF THE PRIOR ART

Other medicinal preparations containing zinc are known, but do not permit the oral administration of zinc in a palatable solution which does not exhibit the characteristic astringent taste of zinc ion. German Offenlegungsschrift No. 2,013,426 discloses insoluble zinc compounds, which have no taste, administered in dragees, insoluble in gastric juice. British Pat. No. 1,029,200, which corresponds to Finnish Pat. No. 42,855, describes a solution of a zinc containing composition for parenteral administration to animals.

The following test was carried out to demonstrate the improvement in palatability achieved by administering a zinc solution in accordance with the present invention, compared with a solution of zinc ion, a solution of zinc ion containing flavouring agents but no complexing agents, and a solution of zinc according to British Pat. No. 1,029,200. The dragees of German OLS No. 2,013,426 were not tested as it is recognized in the art that insoluble compounds have no taste.

In the study a taste panel was used containing of ten healthy volunteers in order to compare four different solutions containing equivalent amounts of zinc.

The four different solutions had the following compositions:

1. Solution containing zinc without flavouring or complexing agents:

| | | |
|---|---|---|
| Zinc sulfate ($ZnSO_4 \cdot 7H_2O$) | 200 mg | |
| Water distilled to | 50 ml | pH = 5.2 |

2. Solution containing zinc and flavouring agents but without complexing agents:

| | | |
|---|---|---|
| Zinc sulfate ($ZnSO_4 \cdot 7H_2O$) | 200 mg | |
| Flavour apple | 12 mg | |
| Saccharin sodium | 10 mg | |
| Water distilled to | 50 ml | pH = 4.9 |

3. Solution containing zinc and a complexing agent, within the scope of the claims of the present application:

| | | |
|---|---|---|
| Zinc sulfate ($ZnSO_4 \cdot 7H_2O$) | 200 mg | |
| Sodium citrate | 400 mg | |
| Water distilled to | 50 ml | pH = 6.7 |

4. Solution according to British Pat. No. 1,029,200, Example 2, but with zinc chloride content reduced to be equivalent in zinc content to 200 mg ZnSO$_4$·7$_2$O per 50 ml:

| | | |
|---|---|---|
| Potassium phosphate dibas. | 200 mg | |
| Sodium phosphate dibas. | 2260 mg | |
| Sodium phosphate monobas. | 4550 mg | |
| Zinc chloride | 94 mg | |
| Tetracemindisodium | 2280 mg | |
| Metagin | 40 mg | |
| Water distilled to | 50 ml | pH = 5.8 |

The taste panel performed four separate tests with a comparison of the following pairs of solutions in each test.

Test I

Solution No. 1 above containing zinc without flavouring or complexing agents.

Solution No. 2 above containing zinc and flavouring agents but without complexing agents.

Test II

Solution No. 1 above containing zinc without flavouring or complexing agents.

Solution No. 3 above containing zinc and a complexing agent.

Test III

Solution No. 2 above containing zinc and flavouring agents but without complexing agents.

Solution No. 3 above containing zinc and a complexing agent.

Test IV

Solution No. 4 above according to British Pat. No. 1,029,200, Example 2, but with zinc chloride content equivalent in zinc content to 200 mg ZnSO$_4$·7H$_2$O per 50 ml.

Solution No. 3 above containing zinc and a complexing agent.

The persons on the panel did not know what they were tasting and the sample solutions were coded and given in random order so that five persons were starting with the first solution of one pair and five persons with the second solution of one pair. Tests I and II were performed with an interval of about 15 minutes and after a pause of four hours tests III and IV were performed with an interval of about 15 minutes. Before each test of a solution the persons on the panel were instructed to rinse their mouths with water.

After testing one pair of solutions the persons on the panel filled a form to describe the taste of each solution, to indicate how the tastes of each pair of solutions were alike and how they differed and to rank the pair of solutions according to how palatable each was with respect to the other solution.

As solution No. 1 was used twice (tests I, II), solution No. 2 twice (tests I, III), solution No. 3 three times (tests II, III, IV) and solution No. 4 once (test IV) in the comparative test the total scores of the palatability were calculated in order to get a comparison of the four different solutions. The calculated scores do not tell the relative differences between the tastes but show the reliability of the ranking order between the four solutions. A translation of the instructions to the persons on the panel is given below.

Translation of instructions given to the persons on the panel

Test I–IV

You have got two bottles each containing 50 ml of solution. The bottles are marked A and B. The content in the bottles are transferred to the plastic cups marked A and B respectively. Before the test the mouth is rinsed with water. Start to taste on A. Spit out the solution and rinse your mouth with water again. Then taste on B. Answer the following questions directly after the test of each pair of solutions.

| | A | B |
|---|---|---|
| 1. Which solution had the best taste | ☐ | ☐ |
| 2. How was the taste | A | B |
| 5 Good | ☐ | ☐ |
| 4 | ☐ | ☐ |
| 3 Acceptable | ☐ | ☐ |
| 2 | ☐ | ☐ |
| 1 Bad | ☐ | ☐ |

3. How would you characterize the taste of the solutions
   A:
   B:
4. In what sense do you think that the solutions were
   (a) different in taste?
   (b) similar in taste?

Results

Test I

Solution No. 1 containing zinc without flavour or complexing agents.

Solution No. 2 containing zinc and flavouring agents but without complexing agents.

1 person preferred the taste of solution No. 1

8 persons preferred the taste of solution No. 2.

1 person considered the tastes of solutions No. 1 and No. 2 to be similar.

The scores given to each solution were distributed in the following way:

| Solution No. 1 | | Solution No. 2 | |
|---|---|---|---|
| Score | Number of Persons | Score | Number of persons |
| 5 Good | | 5 Good | |
| 4 | | 4 | 1 |
| 3 Acceptable | 3 | 3 Acceptable | 5 |
| 2 | 4 | 2 | 4 |
| 1 Bad | 3 | 1 Bad | |
| Average score: 2.0 | | Average score: 2.7 | |

The number of persons using one or more of the different terms for characterization of the taste is given in the brackets.

The taste of solution No. 1 was characterized with the terms below:

| | |
|---|---|
| Bitter, harsh, astringent | (9) |
| Stale, salty, metallic | (3) |
| Neutral | (1) |

The taste of solution No. 2 was characterized with the terms below:

| | |
|---|---|
| Bitter, harsh, astringent | (8) |
| Stale, salty, metallic | (3) |
| Flavoured | (7) |

The solutions were regarded to be different in taste as solution No. 1 was

| | |
|---|---|
| Bitter, harsh, astringent and solution No. 2 was | (1) |
| Flavoured | (8) |

The solutions were regarded to be similar in taste as they were both

| | |
|---|---|
| Bitter, harsh, astringent | (6) |

Test II

Solution No. 1 containing zinc without flavouring or complexing agents.

Solution No. 3 containing zinc and a complexing agent.

1 person preferred the taste of solution No. 1.
8 persons preferred the taste of solution No. 3.
1 person considered the tastes of solution No. 1 and No. 3 to be similar.

The scores given to each solution were distributed in the following way

| Solution No. 1 | | Solution No. 2 | |
|---|---|---|---|
| Score | Number of persons | Score | Number of persons |
| 5 Good | | 5 Good | |
| 4 | | 4 | 5 |
| 3 Acceptable | 2 | 3 Acceptable | 3 |
| 2 | 4 | 2 | 1 |
| 1 Bad | 4 | 1 Bad | 1 |
| Average score: 1.8 | | Average score: 3.2 | |

The number of persons using one or more of the different terms for characterization of the taste is given in the brackets.

The taste solution No. 1 was characterized with the terms below:

| | |
|---|---|
| Bitter, harsh, astringent | (10) |
| Stale, salty, metallic | (3) |

The taste of solution No. 3 was characterized with the terms below:

| | |
|---|---|
| Bitter, harsh, astringent | (3) |
| Stale, salty, metallic | (5) |
| Neutral | (4) |
| Flavoured | (1) |

The solutions were regarded to be different in taste as solution No. 1 was

| | |
|---|---|
| Bitter, harsh, astringent and solution No. 3 was | (7) |
| Stale, salty, metallic | (2) |
| Neutral | (1) |

The solutions were regarded to be similar in taste as they were both

| | |
|---|---|
| Bitter, harsh astringent | (2) |
| Stale, salty, metallic | (2) |

Test III

Solution No. 2 containing zinc and flavouring agents but without complexing agents.

Solution No. 3 containing zinc and a complexing agent.

2 persons preferred the taste of solution No. 2.
8 persons preferred the taste of solution No. 3.

The scores given to each solution were distributed in the following way:

| Solution No. 2 | | Solution No. 3 | |
|---|---|---|---|
| Score | Number of persons | Score | Number of persons |
| 5 Good | | 5 Good | 1 |
| 4 | 1 | 4 | 5 |
| 3 Acceptable | 4 | 3 Acceptable | 4 |
| 2 | 4 | 2 | |
| 1 Bad | 1 | 1 Bad | |
| Average score: 2.5 | | Average score: 3.7 | |

The number of persons using one or more of the different terms for characterization of the taste is given in the brackets.

The taste of solution No. 2 was characterized with the terms below:

| | |
|---|---|
| Bitter, harsh, astringent | (10) |
| Stale, salty, metallic | (1) |
| Flavoured | (6) |

The taste of solution No. 3 was characterized with the terms below:

| | |
|---|---|
| Bitter, harsh, astringent | (1) |
| Stale, salty, metallic | (4) |
| Neutral | (6) |
| Flavoured | (1) |

The solutions were regarded to be different in taste as solution No. 2 was,

| | |
|---|---|
| Bitter, harsh, astringent | (8) |
| Flavoured and solution No. 3 was | (5) |
| Stale, salty, metallic | (1) |
| Neutral | (2) |

The solutions were regarded to be similar in taste as they were both

| Stale, salty, metallic | (3) |
|---|---|

Test IV

Solution No. 4 according to British Pat. No. 1,029,200, Example 2, but with zinc content equivalent to 200 mg ZnSO$_4$·7H$_2$O per 50 ml.

Solution No. 3 containing zinc and a complexing agent.

No person preferred the taste of solution No. 4.

10 persons preferred the taste of solution No. 3.

The scores given to each solution were distributed in the following way:

| Solution No. 4 | | Solution No. 3 | |
|---|---|---|---|
| Score | Number of persons | Score | Number of persons |
| 5 Good | | 5 Good | 1 |
| 4 | | 4 | 4 |
| 3 Acceptable | | 3 Acceptable | 4 |
| 2 | | 2 | 1 |
| 1 Bad | 10 | 1 Bad | |
| Average score: 1.0 | | Average score: 3.5 | |

The number of persons using one or more of the different terms for characterization of the taste is given in the brackets.

The taste of solution No. 4 was characterized with the terms below:

| Stale, salty, metallic | (6) |
|---|---|
| Acidic, burning | (7) |

The taste of solution No. 3 was characterized with the terms below:

| Bitter, harsh, astringent | (1) |
|---|---|
| Stale, salty, metallic | (2) |
| Acidic, burning | (1) |
| Neutral | (5) |
| Flavoured | (1) |

The solutions were regarded to be different in taste as solution No. 4 was

| Stale, salty, metallic | (4) |
|---|---|
| Acidic, burning | (4) |
| and solution No. 3 was | |
| Neutral | (4) |

The solutions were regarded to be similar in taste as they were both

| Acidic, burning | (1) |
|---|---|

The total scores in the comparative test performed in tests I–IV can be summarized in the following figure.

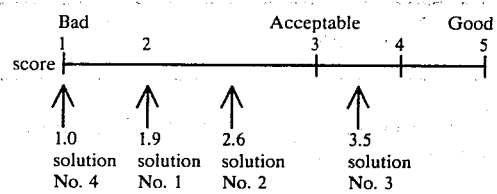

A taste comparison of solutions containing zinc is difficult to perform as the taste of the zinc ion characterized as astringent, harsh and bitter remains for a long period in the oral cavity. Thus there is a great risk of influence of taste between the pair of solutions in a comparative test. This effect was to some degree reduced as the persons on the panel were instructed to rinse their mouths with water before testing each solution.

The persons on the panel were free to characterize the taste of the solutions in as many terms as needed. However, several terms were common for several persons and in order to get a summary of the characterizations the terms were arranged in the following groups.

| Bitter, harsh, astringent | Characteristic for the taste of the free zinc ion |
|---|---|
| Stale, salty, metallic | Characteristic for the taste of salts in water |
| Acidic, burning | Characteristic for the taste of high concentrations of salts in water |
| Neutral | Characteristic for the absence of tastes |
| Flavoured | Characteristic for addition of flavouring agents to the water solutions |

In the comparative test using the panel of ten healthy volunteers there was a clear preference for the taste of the solution containing zinc and a complexing agent (solution No. 3). In the comparisons with the zinc solutions without complexing agents (solutions No. 1 and No. 2) the neutral taste of the solution containing zinc and a complexing agent was pointed out while the bitter, harsh, astringent taste was stressed for the zinc solutions without complexing agents. In the comparison with the solution according to British Pat. No. 1,029,200 (solution No. 4) the neutral taste of the solution containing zinc and a complexing agent was pointed out again.

The addition of flavouring agents to a zinc solution without complexing agent (solution No. 2) cannot eliminate the characteristic bitter, harsh, astringent taste of zinc, though it was considered to be positive for the palatibility of that solution compared to the unflavoured zinc solution without complexing agent (solution No. 1).

The solution according to British Pat. No. 1,029,200, Example 2, but with zinc content reduced to be equivalent to 200 mg ZnSO$_4$·7H$_2$O per 50 ml (solution No. 4) was inferior to all other solutions, even to a solution containing zinc without flavouring or complexing agents (solution No. 1). The solution according to British Pat. No. 1,029,200 was often said to be undrinkable. The bad characterization was reflected in the low score for the palatability of this solution. This means that British Pat. No. 1,029,200 does not suggest that it is possible to obtain a palatable solution of zinc.

U.S. Pat. No. 3,647,834 to Martin discloses the use of zinc mercaptide N-acetylcysteine carboxylates as active ingredients of pharmaceutical preparations and/or cosmetic preparations. However, the '834 patent does not disclose a palatable solution of a complex of a zinc salt and an α-hydroxycarboxylic acid. To evaluate the advantages of the present invention compared to zinc mercaptide N-acetylcysteine carboxylate and more particularly to determine the improvement with regard to taste which is obtained, the following taste comparison was carried out.

In the study a taste panel was used consisting of ten healthy volunteers in order to compare two different solutions containing equivalent amounts of zinc.

The two different solutions had the following compositions:

1. Solution containing zinc citrate complex within the scope of the present application:

| | |
|---|---|
| Zinc sulfate (ZnSO$_4$ . 7H$_2$O) | 200 mg |
| Sodium citrate | 400 mg |
| Water distilled to | 50 ml |
| pH = 7.0 | |

2. Solution containing zinc mercaptide N-acetylcysteine carboxylate in aqueous solution, prepared in accordance with U.S. Pat. No. 3,647,834:

| | |
|---|---|
| Zinc carbonate basic 76 mg is equivalent in zinc content to ZnSO$_4$ . 7H$_2$O 200 mg. | |
| Zinc carbonate basic | 76 mg |
| N-acetyl-L-cysteine | 225 mg |
| Water distilled to | 50 ml |
| pH = 6.5 by addition of sodium hydroxide | |

The persons on the panel did not know what they were tasting and the sample solutions were coded and given in random order so that five persons were starting with the first solution and five persons with the second solution. The tests were performed with an interval of about three hours. Before each test of a solution the persons on the panel were instructed to rinse their mouths with water.

After testing the solutions the persons on the panel filled in a form to describe the taste of each solution, to indicate how the tastes were alike and how they differed and to rank the solutions according to how palatable each was with respect to the other solution. The score of palatability was calculated. The scores do not tell the relative differences between the tastes but show the reliability of the ranking order between the two solutions. A translation of the instructions to the persons on the panel is given below.

Translation of instructions given to the persons on the panel

You have got two bottles each containing 50 ml of solution. The bottles are marked A and B. The contents in the bottles are transferred to the plastic cups marked A and B respectively. Before the test the mouth is rinsed with water. Start to taste on A. Spit out the solution and rinse your mouth with water again. Taste on B after 3 additional hours. Answer the following questions.

| | A | B |
|---|---|---|
| 1. Which solution had the best taste | ☐ | ☐ |
| 2. How was the taste | A | B |
|    5 Good | ☐ | ☐ |
|    4 | ☐ | ☐ |
|    3 Acceptable | ☐ | ☐ |
|    2 | ☐ | ☐ |
|    1 Bad | ☐ | ☐ |
| 3. How would you characterize the taste of the solutions | | |
|    A: | | |
|    B: | | |
| 4. In what sense do you think that the solutions were | | |
|    (a) different in taste? | | |
|    (b) similar in taste? | | |

Results

Solution No. 1 containing zinc citrate complex within the scope of the claims of the present application.

Solution No. 2 containing zinc mercaptide N-acetylcysteine carboxylate according to U.S. Pat. No. 3,647,834.

6 persons preferred the taste of solution No. 1.
4 persons preferred the taste of solution No. 2.

The scores given to each solution were distributed in the following way:

| Solution No. 1 | | Solution No. 2 | |
|---|---|---|---|
| Score | Number of persons | Score | Number of persons |
| 5 Good | | 5 Good | |
| 4 | 2 | 4 | |
| 3 Acceptable | 2 | 3 Acceptable | 3 |
| 2 | 5 | 2 | 2 |
| 1 Bad | 1 | 1 Bad | 3 |
| | | | 2 |
| Average score : 3.5 | | Average score : 2.6 | |

The number of persons using one or more of the different terms for characterization of the taste is given in brackets.

The taste of solution No. 1 was characterized with the terms below:

| | |
|---|---|
| Bitter, harsh | (3) |
| Stale, salty, metallic | (5) |
| Neutral | (6) |
| Flavoured | (1) |

The taste of solution No. 2 was characterized with the terms below:

| | |
|---|---|
| Bitter, harsh | (4) |
| Stale, salty, metallic | (5) |
| Neutral | (2) |
| Flavoured | (6) |
| Taste of amino acid, meat, gelatin, sulfur | (5) |

The solutions were regarded to be different in taste as solution

| | |
|---|---|
| No. 1 was | |
| Bitter | (1) |
| Salty | (2) |

-continued

| Neutral | (2) |
|---|---| and solution No. 2 was

| Bitter, harsh | (3) |
|---|---|
| Stale, metallic | (2) |
| Neutral | (1) |
| Flavoured | (2) |
| Taste of amino acid, meat | (1) |

The solutions were regarded to be similar in taste as they were both

| Stale, salty, metallic | (2) |
|---|---|
| Neutral | (2) |

The scores in the comparative test can be summarized in the following figure:

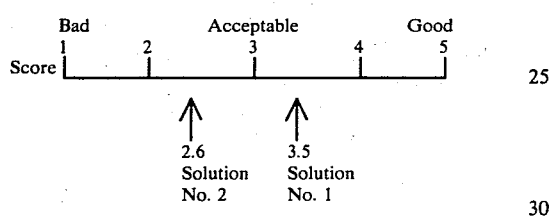

As there were only two solutions to be tested, the effect of the astringent zinc taste remaining in the oral cavity could be reduced by instructing the persons on the panel not to test the second solution until three hours after the first solution.

The persons on the panel were free to characterize the taste of the solutions in as many terms as needed. However, several terms were common for several persons and in order to get a summary of the characterizations the terms were arranged in the following groups.

| Bitter, harsh, astringent | Characteristic for the taste of the free zinc ion. |
|---|---|
| Stale, salty, metallic | Characteristic for the taste of salts in water. |
| Neutral | Characteristic for the absence of tastes. |
| Flavoured | Characteristic for the addition of flavouring agents to the water solutions. |
| Aminoacid, meat, gelatin, suflur | Characteristic for aminoacids, the latter especially for those containing sulfur atoms. |

In the comparative test using the panel of ten healthy volunteers there was a preference for the taste of the solution containing zinc and the complexing agent citrate (solution No. 1) according to the present application.

The neutral taste of the solution containing zinc and the complexing agent citrate was pointed out, while the taste of sulfur-containing aminoacid was stressed for the zinc solution containing mercaptide N-acetylcysteine carboxylate (solution No. 2) according to U.S. Pat. No. 3,647,834. The solution containing zinc mercaptide N-acetylcysteine carboxylate was given a low score for the palatability of the solution. Although the use of U.S. Pat. No. 3,647,834 provides an improved taste for N-acetylcysteine, there is still a taste of the sulfur-containing aminoacid which makes it not acceptable in order to achieve palatable solutions of zinc.

EXAMPLES

The present invention will be described more in detail in the Examples below, without being restricted thereto.

EXAMPLE 1

| Zinc sulphate pulverulent | 0.100 kg |
|---|---|
| Sorbitol | 0.400 kg |
| Sodium bicarbonate | 0.300 kg |
| Citric acid | 0.400 kg |
| Flavouring agents | q.s. |

After drying the ingredients are mixed and the mass is tabletted in a tabletting machine for effervescent tablets having self-lubricating punches. Each effervescent tablet contains 40 mg of zinc and is dissolved in 100 ml of water prior to administration. The pH is 4.3. The beverage obtained is good tasting.

EXAMPLE 2

| Zinc sulphate pulverulent | 0.125 kg |
|---|---|
| Sugar | 4.000 kg |
| Tartaric acid | 0.700 kg |
| Sodium bicarbonate | 0.600 kg |
| Flavoring agents | q.s. |

The pulverulent substances are dried and well mixed and packed in tight bags each containing zinc corresponding to 45 mg and intended to be dissolved in 100 ml of water. The contents of one bag are dissolved in water immediately before administration and give thereby a good tasting beverage. The pH is 4.3.

EXAMPLE 3

| Zinc chloride | 0.094 kg |
|---|---|
| Sugar | 0.400 kg |
| Citric acid | 0.400 kg |
| Sodium hydroxide to pH 4.5 | q.s. |
| Flavoring agents | q.s. |
| Water to | 100 liters |

The zinc chloride, sugar, citric acid, and flavoring agents are dissolved in the main part of the water, whereupon the pH is adjusted to 4.5 using sodium hydroxide. The remaining amount of water is added to final volume, whereupon the solution is dispensed. 100 ml of solution correspond to 45 mg of zinc.

EXAMPLE 4

| zinc sulphate, pulverulent | 0.125 kg |
|---|---|
| Sorbitol | 0.400 kg |
| Sodium bicarbonate | 0.200 kg |
| Sodium dihydrogen citrate | 0.400 kg |
| Flavoring agents | q.s. |

After having been dried the ingredients are mixed and the mass is tabletted in a tabletting machine for effervescent tablets provided with special punches. Each tablet contains 45 mg of zinc and is dissolved in 100 ml of water prior to administration. The pH is thereby 5.2. The drink obtained is good tasting.

EXAMPLE 5

| | |
|---|---|
| Zinc sulphate, pulverulent | 0.125 kg |
| Sorbitol | 0.400 kg |
| Sodium bicarbonate | 0.300 kg |
| Malic acid | 0.350 kg |
| Flavoring agents | q.s. |

After drying, the ingredients are mixed and the mass is tabletted in a tabletting machine for effervescent tablets having self-lubricating punches. Each effervescent tablet contains 45 mg of zinc, and is dissolved in 100 mls of water prior to administration. The pH of the resulting solution is 4.8. The beverage obtained is good tasting.

EXAMPLE 6

| | |
|---|---|
| Zinc sulphate (. 7H$_2$O) | 0.200 kg |
| Sugar | 0.400 kg |
| Glycolic acid | 0.400 kg |
| Sodium hydroxide to pH 5.1 | q.s. |
| Flavoring agents | q.s. |
| Water to | 100 liters |

The zinc sulphate, sugar, glycolic acid and flavoring agents are dissolved in the main portion of the water. The pH is adjusted to 5.1 and the remaining water is added. There are 45 mg of zinc in 100 mls of this solution.

EXAMPLE 7

| | |
|---|---|
| Zinc chloride | 0.094 kg |
| Sugar | 0.400 kg |
| Lactic acid | 0.400 kg |
| Sodium hydroxide to pH 5.1 | q.s. |
| Flavoring agents | q.s. |
| Water to | 100 liters |

Zinc chloride, sugar, lactic acid and flavoring agents are dissolved in the main portion of the water. The pH is adjusted to 5.1, and the remaining water is added. There are 45 mg of zinc in 100 ml of solution.

In a solution of the above preparations zinc is present bound as a complex with the carboxylic acid at the given pH. At the time of administration however, a pH change occurs in the stomach, whereby the complex is dissolved and free zinc ions appear which can easily be resorbed through the gastro-intestinal mucosa and be taken up by the blood. By means of the complex formation the astringent taste of the zinc is concealed and good tasting, drinkable solutions are obtained. The zinc complex can also be produced in dry form and be incorporated as such in the preparation.

The flavor of the solutions may also be further varied by different flavoring agents such as sugar and fruit essences in accordance with the examples above. In case effervescent preparations are present the carbon dioxide gives a positive effect as regards the taste.

We claim:

1. In the treatment of zinc deficiency in mammals, including humans, by administering zinc gastrointestinally, the improvement which comprises administering zinc orally in the form of a palatable aqueous solution containing a zinc salt and a complex-forming carboxylic acid selected from the group consisting of citric acid, tartaric acid, malic acid, lactic acid, and glycolic acid, and acid anhydrides and salts thereof, the relation of complex former to zinc being at least equimolecular and the amount of zinc being 3 to 500 mg per peroral dose, the pH of the solution being in the range of 3 to 9.

2. The method of claim 1 wherein the zinc salt is selected from the group consisting of zinc chloride, zinc nitrate, zinc sulphate, zinc acetate, and zinc carbonate.

3. The method of claim 1 wherein the pH of the solution is regulated to a pH in the range 3 to 6.

4. The method of claim 1 wherein the solution is a carbonated aqueous solution.

5. The method of claim 1 wherein the solution is a non-carbonated aqueous solution.

* * * * *

UNITED STATES PATENT AND TRADEMARK OFFICE
CERTIFICATE OF CORRECTION

PATENT NO. : 4,292,324

DATED : September 29, 1981

INVENTOR(S) : Karl E. Jonsson and Nils F.E. Moren

It is certified that error appears in the above—identified patent and that said Letters Patent is hereby corrected as shown below:

Title page, 4th line of Item 63, "71,720" should read -- 571,720 --.

Column 2, line 40, "containing" should read -- consisting --.

Signed and Sealed this

Twenty-seventh Day of April 1982

|SEAL|

Attest:

GERALD J. MOSSINGHOFF

Attesting Officer

Commissioner of Patents and Trademarks